(12) United States Patent  (10) Patent No.: US 6,706,055 B2
Douk et al.  (45) Date of Patent: Mar. 16, 2004

(54) GUIDEWIRE APPARATUS FOR TEMPORARY DISTAL EMBOLIC PROTECTION

(75) Inventors: Nareak Douk, Lowell, MA (US); Nasser Rafiee, Andover, MA (US); David J. Sauvageau, Metheun, MA (US); Steve Dapolito, Brookline, NH (US)

(73) Assignee: Medtronic Ave Inc., Santa Rosa, CA (US)

( * ) Notice: Subject to any disclaimer, the term of this patent is extended or adjusted under 35 U.S.C. 154(b) by 0 days.

(21) Appl. No.: 10/351,634

(22) Filed: Jan. 24, 2003

(65) Prior Publication Data

US 2003/0135232 A1 Jul. 17, 2003

Related U.S. Application Data

(63) Continuation-in-part of application No. 10/099,399, filed on Mar. 15, 2002, which is a continuation-in-part of application No. 09/918,441, filed on Jul. 27, 2001, which is a continuation-in-part of application No. 09/824,832, filed on Apr. 3, 2001.

(51) Int. Cl.[7] ............................................. A61M 29/00
(52) U.S. Cl. ..................................................... 606/200
(58) Field of Search ................................. 606/200, 113, 606/114, 127, 159

(56) References Cited

U.S. PATENT DOCUMENTS

| | | |
|---|---|---|
| 3,554,050 A | 1/1971 | Conrad |
| 3,996,938 A | 12/1976 | Clark, III |
| 4,300,408 A | 11/1981 | Yoshifuji |
| 4,650,466 A | 3/1987 | Luther |
| 4,771,782 A | 9/1988 | Millar |
| 4,824,435 A | 4/1989 | Giesy et al. |
| 4,885,003 A | 12/1989 | Hillstead |
| 4,921,484 A | 5/1990 | Hillstead |
| 5,002,560 A | 3/1991 | Machold et al. |
| 5,040,548 A | 8/1991 | Yock |
| 5,041,093 A | 8/1991 | Chu |
| 5,161,427 A | 11/1992 | Fukuda et al. |
| 5,245,887 A | 9/1993 | Tanaka et al. |
| 5,421,832 A | 6/1995 | Lefebvre |
| 5,451,233 A | 9/1995 | Yock |
| 5,569,184 A | 10/1996 | Crocker et al. |

(List continued on next page.)

FOREIGN PATENT DOCUMENTS

| | | |
|---|---|---|
| EP | 1 123 688 A2 | 8/2001 |
| WO | WO 96/01591 A1 | 1/1996 |
| WO | WO 99/22673 A1 | 5/1999 |
| WO | WO 99/58068 A2 | 11/1999 |
| WO | WO 0145592 | 6/2001 |
| WO | WO 01/49215 A2 | 7/2001 |
| WO | WO 01/80776 A1 | 11/2001 |

Primary Examiner—Kevin T. Truong

(57) ABSTRACT

A guidewire apparatus for use during percutaneous catheter interventions such as angioplasty or stent deployment. A protection element comprising a filter or an occluder is mounted near the distal end of a steerable guidewire, which guides a therapeutic catheter. The guidewire apparatus comprises a hollow shaft movably disposed about a core wire. The shaft and core wire control relative displacement of the ends of the protection element, causing transformation of the protection element between a deployed configuration and a collapsed configuration. The protection element is freely rotatable about the guidewire apparatus. A tracking member disposed adjacent the distal end of the guidewire apparatus can be used to guide the device along another guidewire. Thrust bearings may be employed to facilitate unlimited rotation of the steerable guidewire within the protection element, especially while the protection element is retained in the collapsed configuration.

17 Claims, 8 Drawing Sheets

U.S. PATENT DOCUMENTS

| | | |
|---|---|---|
| 5,578,009 A | 11/1996 | Kraus et al. |
| 5,695,469 A | 12/1997 | Segal |
| 5,749,888 A | 5/1998 | Yock |
| 5,769,868 A | 6/1998 | Yock |
| 5,910,154 A | 6/1999 | Tsugita et al. |
| 5,911,734 A | 6/1999 | Tsugita et al. |
| 5,925,060 A | 7/1999 | Forber |
| 5,972,019 A | 10/1999 | Engelson et al. |
| 6,066,158 A | 5/2000 | Engelson et al. |
| 6,142,987 A | 11/2000 | Tsugita |
| 6,146,396 A | 11/2000 | Konya et al. |
| 6,179,859 B1 * | 1/2001 | Bates et al. .................. 606/200 |
| 6,245,089 B1 | 6/2001 | Daniel et al. |
| 6,258,115 B1 | 7/2001 | Dubrul |
| 6,325,815 B1 | 12/2001 | Kusleika et al. |
| 6,511,496 B1 * | 1/2003 | Huter et al. .................. 606/200 |
| 2001/0041908 A1 | 11/2001 | Levinson et al. |

* cited by examiner

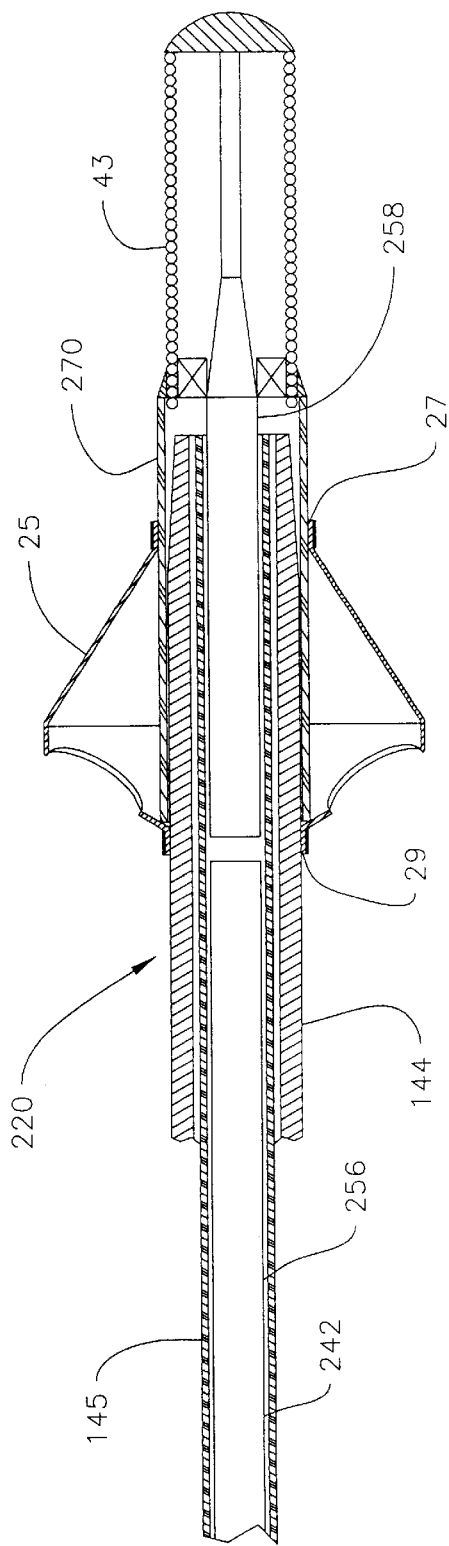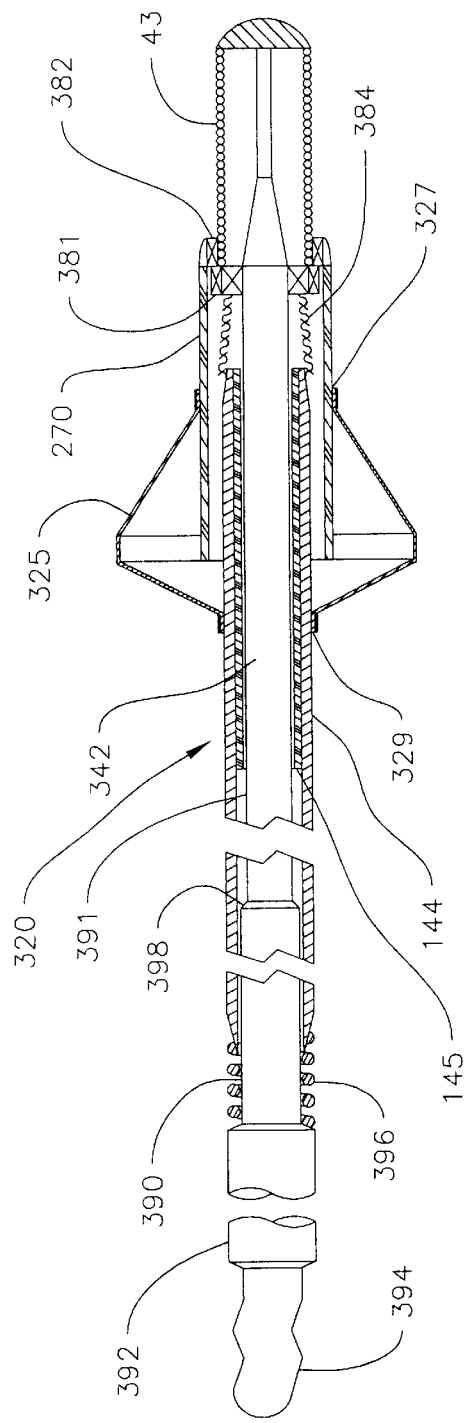

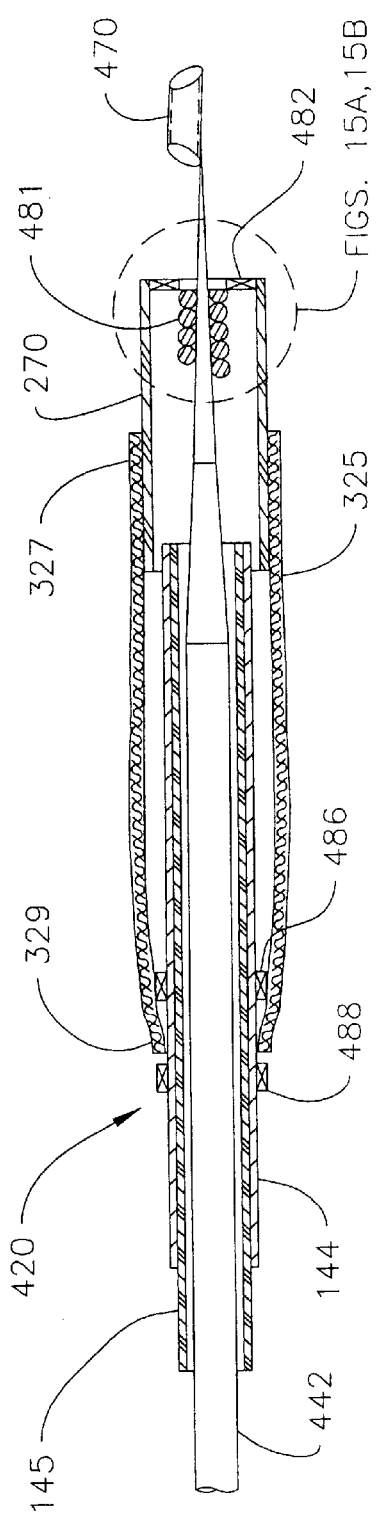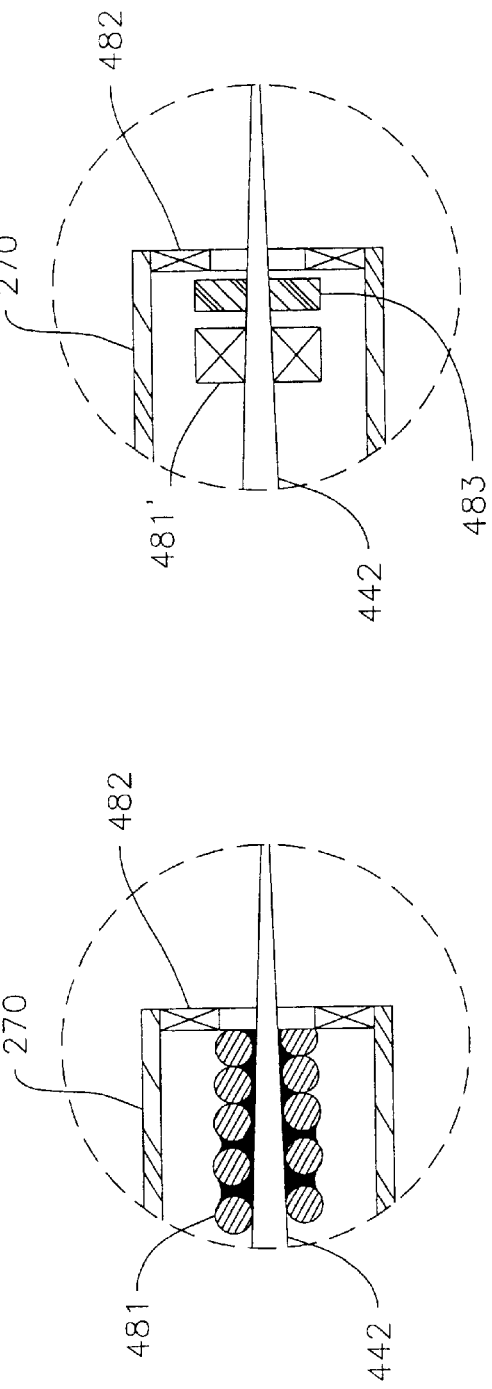
FIG. 14
FIG. 15A
FIG. 15B

GUIDEWIRE APPARATUS FOR TEMPORARY DISTAL EMBOLIC PROTECTION

CROSS-REFERENCE TO RELATED APPLICATIONS

This patent application is a continuation-in-part of U.S. patent application Ser. No. 10/099,399 to Douk et al. filed Mar. 15, 2002 now pending, which is a continuation-in-part of U.S. patent application Ser. No. 09/918,441 to Douk et al. filed Jul. 27, 2001, now pending, which is a continuation-in-part of U.S. patent application Ser. No. 09/824,832 to Douk et al. filed Apr. 3, 2001 now pending, entitled "Temporary Intraluminal Filter Guidewire and Methods of Use."

FIELD OF THE INVENTION

The present invention relates generally to intraluminal devices for capturing particulate in the vessels of a patient. More particularly, the invention relates to a filter or an occluder for capturing emboli in a blood vessel during an interventional vascular procedure, then removing the captured emboli from the patient after completion of the procedure. Furthermore, the invention concerns a filter or an occluder mounted on a guidewire that can also be used to direct an interventional catheter to a treatment site within a patient.

BACKGROUND OF THE INVENTION

A variety of treatments exists for dilating or removing atherosclerotic plaque in blood vessels. The use of an angioplasty balloon catheter is common in the art as a minimally invasive treatment to enlarge a stenotic or diseased blood vessel. When applied to the vessels of the heart, this treatment is known as percutaneous transluminal coronary angioplasty, or PTCA. To provide radial support to the treated vessel in order to prolong the positive effects of PTCA, a stent may be implanted in conjunction with the procedure.

Thrombectomy is a minimally invasive technique for removal of an entire thrombus or a sufficient portion of the thrombus to enlarge the stenotic or diseased blood vessel and may be accomplished instead of a PTCA procedure. Atherectomy is another well-known minimally invasive procedure that mechanically cuts or abrades a stenosis within the diseased portion of the vessel. Alternatively, ablation therapies use laser or RF signals to superheat or vaporize a thrombus within the vessel. Emboli loosened during such procedures may be removed from the patient through the catheter.

During each of these procedures, there is a risk that emboli dislodged by the procedure will migrate through the circulatory system and cause ischaemic events, such as infarction or stroke. Thus, practitioners have approached prevention of escaped emboli through use of occlusion devices, filters, lysing, and aspiration techniques. For example, it is known to remove the embolic material by suction through an aspiration lumen in the treatment catheter or by capturing emboli in a filter or occlusion device positioned distal of the treatment area.

SUMMARY OF THE INVENTION

The guidewire apparatus of the invention includes a protection element comprising a filter or an occluder mounted near the distal end of a steerable guidewire, which guides a therapeutic catheter. The guidewire apparatus comprises a hollow shaft movably disposed about a core wire and, optionally, a slippery liner interfitted there between. The shaft and core wire control relative displacement of the ends of the protection element, causing transformation of the protection element between a deployed configuration and a collapsed configuration. The protection element is freely rotatable about the guidewire apparatus. A tracking member disposed adjacent the distal end of the guidewire apparatus can be used to guide the device along another guidewire. Thrust bearings may be employed to facilitate unlimited rotation of the steerable guidewire within the protection element, especially while the protection element is retained in the collapsed configuration.

BRIEF DESCRIPTION OF THE DRAWINGS

Features, aspects and advantages of the present invention will become better understood with reference to the following description, appended claims, and accompanying drawings where:

FIG. 12 is a partially sectioned longitudinal view of a third guidewire embodiment in accordance with the invention; and FIG. 13 is a partially sectioned longitudinal view of a fourth guidewire embodiment in accordance with the invention;

FIG. 14 is a partially sectioned longitudinal view of a fifth guidewire embodiment in accordance with the invention;

FIG. 15A is an enlarged view of a stop element assembly shown in FIG. 14;

FIG. 15B is an enlarged view of a modified form of the stop element assembly shown in FIG. 14.

DETAILED DESCRIPTION OF THE INVENTION

Figure 1:
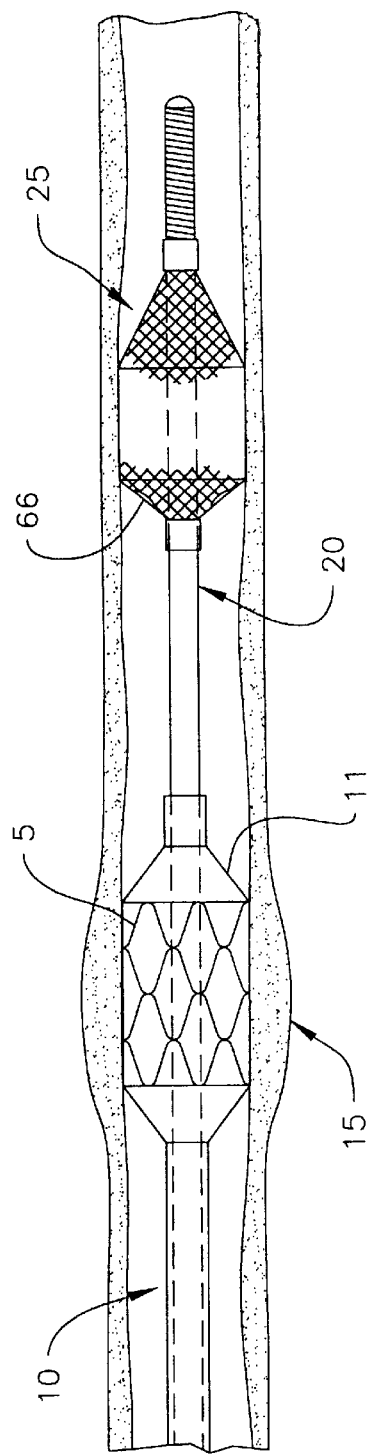
FIG. 1 is an illustration of a filter system in accordance with the invention deployed within a blood vessel.
Figure 2:
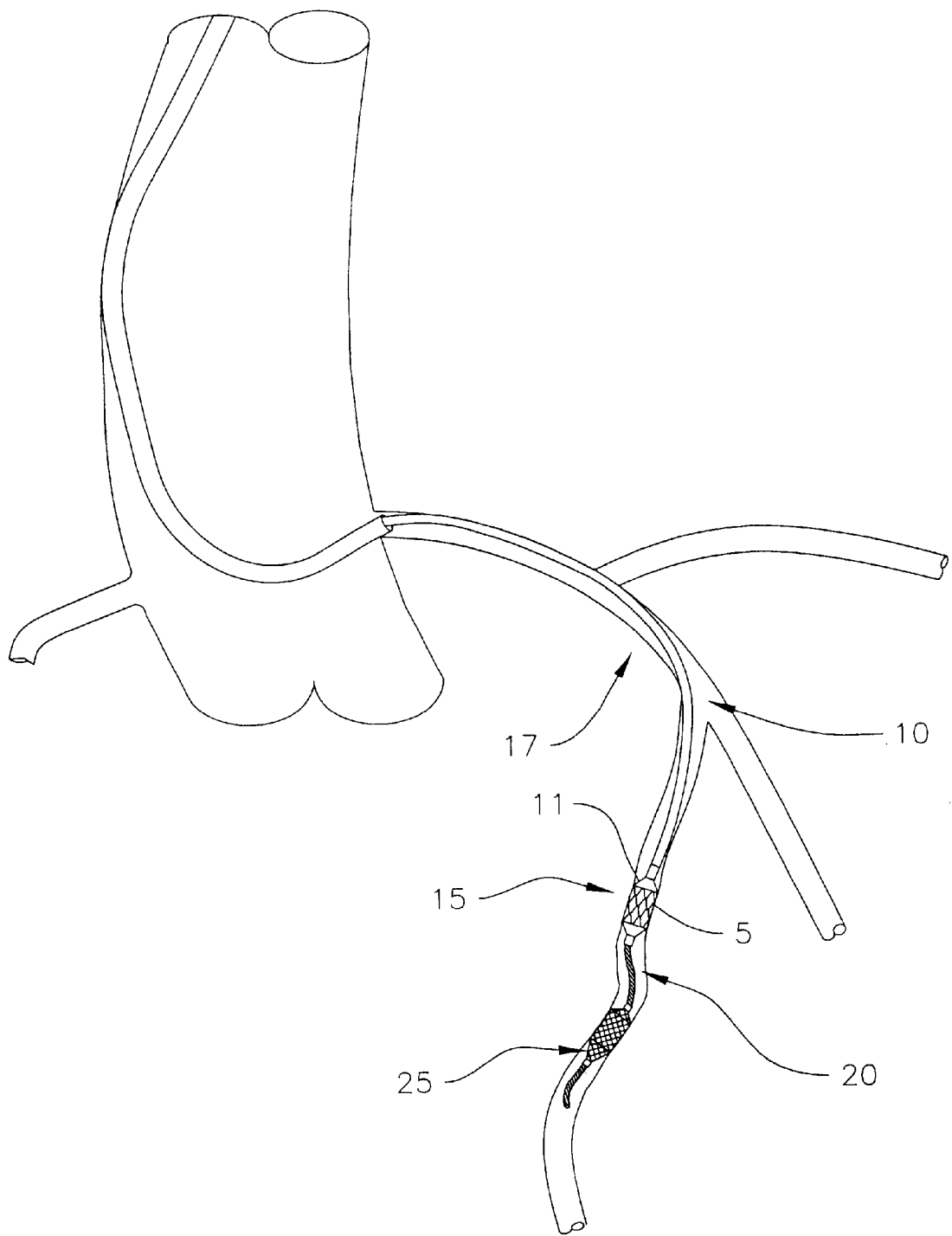
FIG. 2 is an illustration of a filter system in accordance with the invention deployed within a portion of the coronary arterial anatomy.

The present invention is a guidewire apparatus for use in minimally invasive procedures. While the following description of the invention relates to vascular interventions, it is to be understood that the invention is applicable to other procedures where the practitioner desires to capture embolic material that may be dislodged during the procedure. Intravascular procedures such as PTCA or stent deployment are often preferable to more invasive surgical techniques in the treatment of vascular narrowings, called stenoses or lesions. With reference to FIGS. 1 and 2, deployment of balloon expandable stent 5 is accomplished by threading catheter 10 through the vascular system of the patient until stent 5 is located within a stenosis at predetermined treatment site 15. Once positioned, balloon 11 of catheter 10 is inflated to expand stent 5 against the vascular wall to maintain the opening. Stent deployment can be performed following treatments such as angioplasty, or during initial balloon dilation of the treatment site, which is referred to as primary stenting.

Catheter 10 is typically guided to treatment site 15 by a guidewire. In cases where the target stenosis is located in tortuous vessels that are remote from the vascular access point, such as coronary arteries 17 shown in FIG. 2, a steerable guidewire is commonly used. According to the present invention, a guidewire apparatus generally guides catheter 10 to treatment site 15 and includes a distally disposed protection element to collect embolic debris that may be generated during the procedure. Various embodiments of the invention will be described as either filter guidewires or occluder guidewires. However, it is to be understood that filters and occluders are interchangeable types of protection elements among the inventive structures disclosed. The invention is directed to embolic protection elements wherein relative movement of the ends of the protection element either causes or accompanies transformation of the element between a collapsed configuration and an expanded, or deployed configuration. Such transformation may be impelled by external mechanical means or by self-shaping memory (either self-expanding or self-collapsing) within the protection element itself. The protection element may be self-expanding, meaning that it has a mechanical memory to return to the expanded, or deployed configuration. Such mechanical memory can be imparted to the metal comprising the element by thermal treatment to achieve a spring temper in stainless steel, for example, or to set a shape memory in a susceptible metal alloy such as a nickel-titanium (nitinol) alloy.

Filter guidewires in accordance with the invention include distally disposed filter 25, which may comprise a tube formed by braided filaments that define pores and have at least one proximally-facing inlet opening 66 that is substantially larger than the pores. Alternative types of filters may be used in filter 25, such as filter assemblies that include a porous mesh mounted to expandable struts. Optionally, adding radiopaque markers to filter ends 27, 29, as shown in FIG. 12, can aid in fluoroscopic observation of filter 25 during manipulation thereof. Alternatively, to enhance visualization of braided filter 25 under fluoroscopy, at least one of the filaments may be a wire having enhanced radiopacity compared to conventional non-radiopaque wires suitable for braiding filter 25. At least the majority of braiding wires forming filter 25 should be capable of being heat set into the desired filter shape, and such wires should also have sufficient elastic properties to provide the desired self-expanding or self-collapsing features. Stainless steel and nitinol monofilaments are suitable for braiding filter 25. A braiding wire having enhanced radiopacity may be made of, or coated with, a radiopaque metal such as gold, platinum, tungsten, alloys thereof, or other biocompatible metals that, compared with stainless steel or nitinol, have a relatively high X-ray attenuation coefficient. One or more filaments having enhanced radiopacity may be inter-woven with non-radiopaque wires, or all wires comprising filter 25 may have the same enhanced radiopacity.

Figure 3:
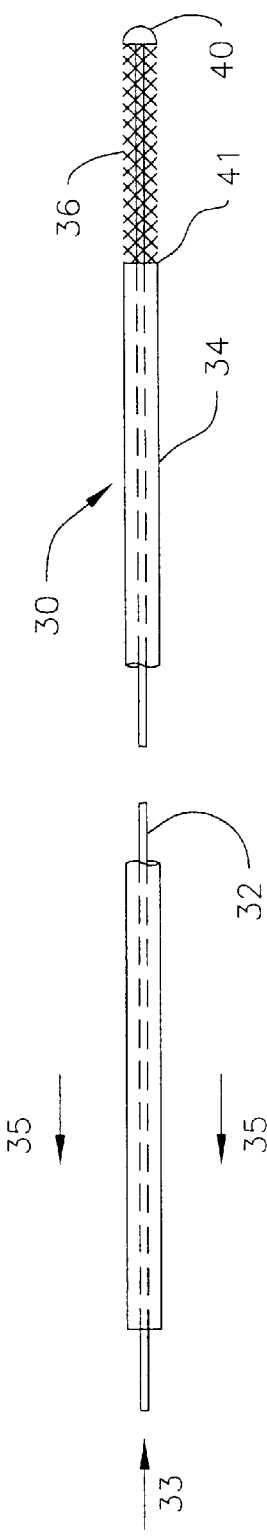
FIG. 3 is an illustration of a prior art expandable mesh device, shown with the mesh in a collapsed configuration.
Figure 4:
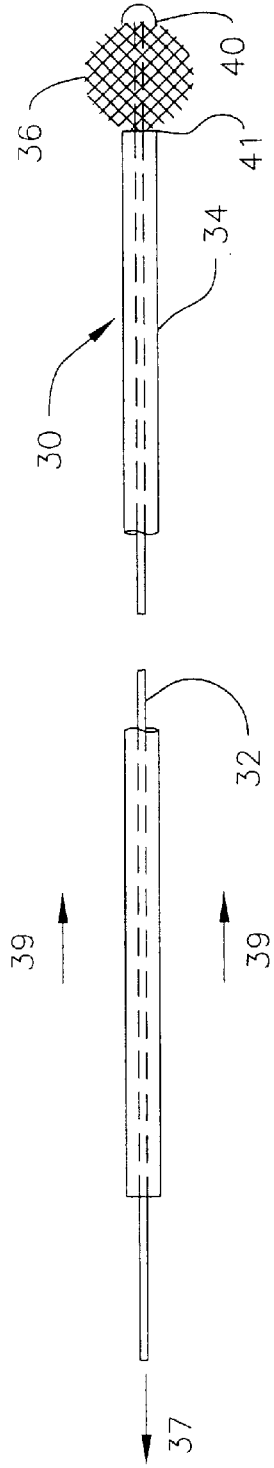
FIG. 4 is an illustration of a prior art expandable mesh device, shown with the mesh in a deployed configuration.

In accordance with the invention, maintaining filter 25 in a collapsed configuration during introduction and withdrawal of filter guidewire 20 does not require a control sheath that slidingly envelops filter 25. Thus, this type of device is sometimes termed as "sheathless." Known types of sheathless vascular filter devices are operated by a push-pull mechanism that is also typical of other expandable braid devices, as shown in FIGS. 3 and 4. Prior art expandable mesh device 30 includes core wire 32 and hollow shaft 34 movably disposed there about. Tubular mesh, or braid 36 surrounds core wire 32 and has a braid distal end fixed to core wire distal end 40 and a braid proximal end fixed to shaft distal end 41. To expand braid 36, core wire 32 is pulled and shaft 34 is pushed, as shown by arrows 37 and 39 respectively in FIG. 4. The relative displacement of core wire 32 and shaft 34 moves the ends of braid 36 towards each other, forcing the middle region of braid 36 to expand. To collapse braid 36, core wire 32 is pushed and shaft 34 is pulled, as shown by arrows 33 and 35 respectively in FIG. 3. This reverse manipulation draws the ends of braid 36 apart, pulling the middle region of braid 36 radially inward toward core wire 32.

Figure 5:
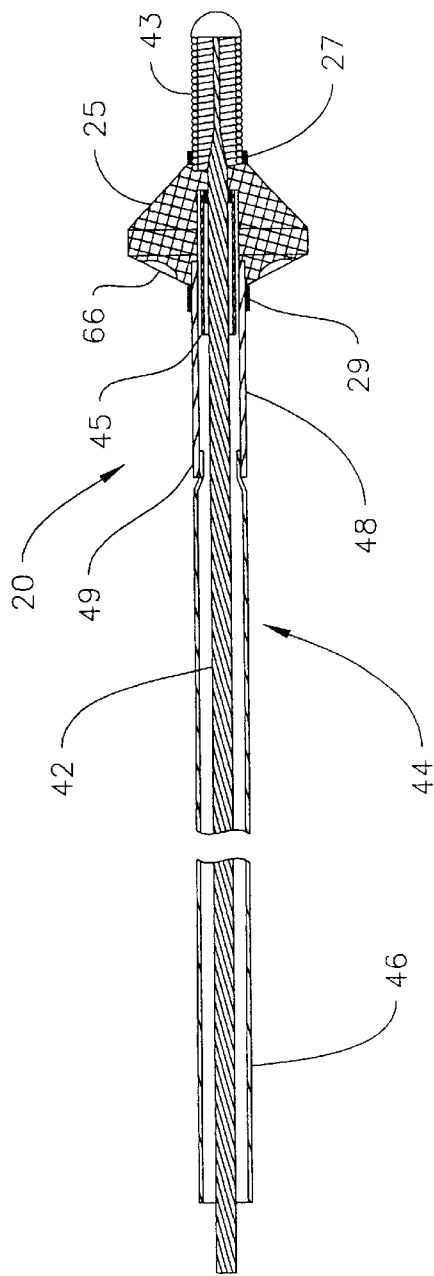
FIG. 5 is a longitudinal sectional view of a first guidewire embodiment in accordance with the invention.

Referring now to FIG. 5, in a first embodiment of the invention, filter guidewire 20 includes core wire 42 and flexible tubular tip member 43, such as a coil spring, fixed around the distal end of core wire 42. Thin wires made from stainless steel and/or one of various alloys of platinum are commonly used to make coil springs for such use in guidewires. Core wire 42 can be made from shape memory metal such as nitinol, or a stainless steel wire, and is typically tapered at its distal end. For treating small caliber vessels such as coronary arteries, core wire 42 may measure about 0.15 mm (0.006 inch) in diameter.

In filter guidewire 20, hollow shaft 44 is movably disposed around core wire 42, and includes relatively stiff proximal portion 46 and relatively flexible distal portion 48. Proximal portion 46 may be made from thin walled stainless steel tubing, usually referred to as hypo tubing, although other metals, such as nitinol, can be used. Various metals or polymers can be used to make relatively flexible distal portion 48. One appropriate material for this element is thermoset polyimide (PI) tubing, available from sources such as HV Technologies, Inc., Trenton, Ga., U.S.A. The length of distal portion 48 may be selected as appropriate for the intended use of the filter guidewire. In one example, portion 48 may be designed and intended to be flexible enough to negotiate tortuous coronary arteries, in which case the length of portion 48 may be 15–35 cm (5.9–13.8 inches), or at least approximately 25 cm (9.8 inches). In comparison to treatment of coronary vessels, adaptations of the invention for treatment of renal arteries may require a relatively shorter flexible portion 48, and neurovascular versions intended for approaching vessels in the head and neck may require a relatively longer flexible portion 48.

When filter guidewire 20 is designed for use in small vessels, shaft 44 may have an outer diameter of about 0.36 mm (0.014 inch). The general uniformity of the outer diameter may be maintained by connecting proximal portion 46 and distal portion 48 with lap joint 49. Lap joint 49, and all other adhesive joints in the invention, may use any suitable biocompatible adhesive such as ultraviolet (UV) light curable adhesives, thermally curable adhesives or so-called "instant" cyanoacrylate adhesives from Dymax Corporation, Torrington, Conn., U.S.A or Loctite Corporation, Rocky Hill, Conn., U.S.A. Lap joint 49 can be formed by any conventional method such as reducing the wall thickness of proximal portion 46 in the region of joint 49, or by forming a step-down in diameter at this location with negligible change in wall thickness, as by swaging.

Expandable tubular filter 25 is positioned generally concentrically with core wire 42, and is sized such that when it is fully deployed, as shown in FIGS. 1 and 2, the outer perimeter of filter 25 will contact the inner surface of the vessel wall. The surface contact is maintained around the entire vessel lumen to prevent any emboli from slipping past filter 25. Adhesive may be used to secure filter distal end 27 to tip member 43, and to secure filter proximal end 29 near the distal end of shaft 44. As shown in FIGS. 12 and 13, radiopaque marker bands, such as platinum rings, can be incorporated into the adhesive joints securing filter ends 27, 29 respectively to tip member 43 and shaft 44. Filter 25 is deployed by advancing, or pushing shaft 44 relative to core wire 42 such that filter distal and proximal ends 27, 29 are drawn toward each other, forcing the middle, or central section of filter 25 to expand radially. Filter 25 is collapsed by withdrawing, or pulling shaft 44 relative to core wire 42 such that filter distal and proximal ends 27, 29 are drawn apart from each other, forcing the middle, or central section of filter 25 to contract radially.

Transition sleeve 45 is fixed about core wire 42 and is slidably located within the distal end of flexible distal portion 48 of hollow shaft 44. Transition sleeve 45 may be made of polyimide tubing similar to that used in distal portion 48 and extends distally there from. By partially filling the annular space between core wire 42 and shaft 44, and by contributing additional stiffness over its length, sleeve 45 supports core wire 42 and provides a gradual transition in overall stiffness of filter guidewire 20 adjacent the distal end of shaft 44. Transition sleeve 45 is fixed to core wire 42 with a suitable adhesive, such that relative displacement between shaft 44 and core wire 42 causes corresponding relative displacement between shaft 44 and sleeve 45. The length and mounting position of sleeve 45 are selected such that sleeve 45 spans the distal end of shaft 44 regardless of the configuration of filter 25 and the corresponding position of shaft 44 relative to core wire 42. When constructed as described above, filter guidewire 20 provides the functions of a temporary filter combined with the performance of a steerable guidewire.

Figure 6:
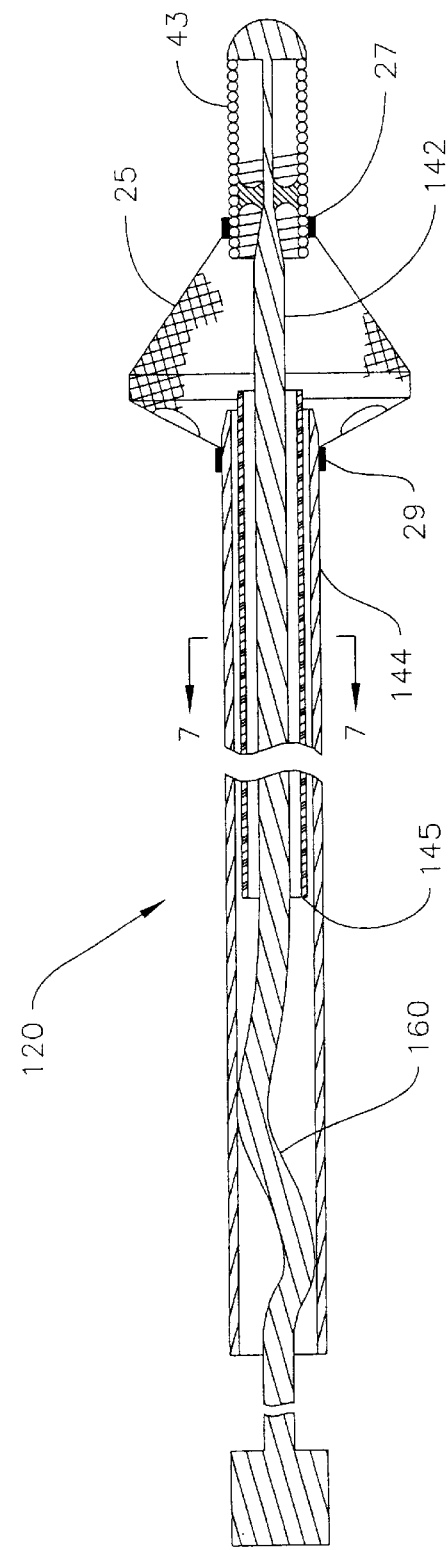
FIG. 6 is a longitudinal sectional view of a second guidewire embodiment in accordance with the invention.

FIG. 6 depicts a second embodiment of the invention in which filter guidewire 120 incorporates a number of elements similar to the elements that make up filter guidewire 20. Such similar elements will be identified with the same reference numerals throughout the description of the invention. Filter guidewire 120 includes core wire 142 and flexible tubular tip member 43 fixed around the distal end of core wire 142, similar to the arrangement of guidewire 20, above. Hollow shaft 144 is movably disposed around core wire 142 and is comparable, throughout its length, to relatively stiff proximal portion 46 of filter guidewire 20. Filter 25 is positioned generally concentrically with core wire 142. Filter distal end 27 is fixedly coupled to tip member 43, and filter proximal end 29 is fixedly coupled near the distal end of shaft 144.

Optionally, a portion of core wire 142 within the proximal end of shaft 144 has one or more bends 160 formed therein. The amplitude, or maximal transverse dimension of bends 160 is selected such that the bent portion of core wire 142 fits, with interference, within shaft 144. The interference fit provides sufficient friction to hold core wire 142 and shaft 144 in desired axial positions relative to each other, thereby controlling the shape of filter 25, as described above with respect to filter guidewire 20.

In filter guidewire 120, liner 145 is interfitted as a low-friction axial bearing in the annular space between core wire 142 and shaft 144. With respect to the three coaxially arranged elements, the selected dimensions and the stack-up of dimensional tolerances will determine how liner 145 functions during the push-pull operation of core wire 142 within shaft 144.

Figure 7:
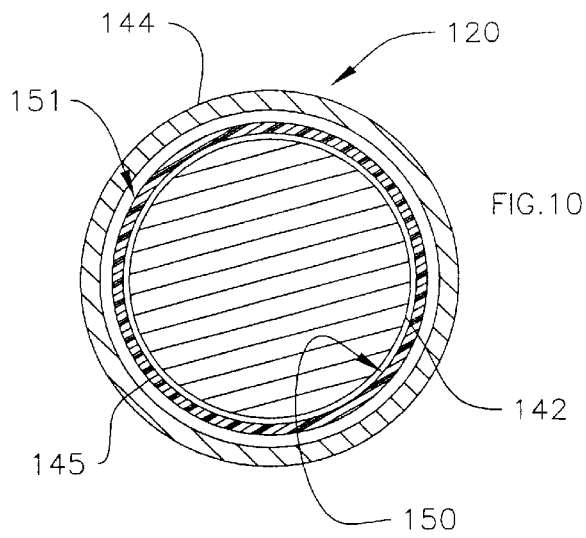
FIG. 7 is a cross-sectional view of the second guidewire embodiment taken along the lines 7—7 of FIG. 6.

For example, FIG. 7 depicts a cross-section of filter guidewire 120 in which there is radial clearance between liner inner surface 150 and core wire 142, and there is also radial clearance between liner outer surface 151 and the inner wall of shaft 144. In this arrangement, liner 145 is radially free-floating in the annular space between core wire 142 and shaft 144. The length of liner 145 is selected such that it also "floats" axially along core wire 142. The axial movement of liner 145 along core wire 142 is limited proximally by a stop formed at the engagement of bends 160 with the inner wall of shaft 144. Tip member 43 limits the axial distal movement of liner 145 along core wire 142. The radial and axial flotation of liner 145 in filter guidewire 120 provides an axial bearing wherein the components with the lesser relative coefficient of friction can slide against each other. For example, if the coefficient of friction between liner inner surface 150 and core wire 142 is less than the coefficient of friction between liner outer surface 151 and the inner wall of shaft 144, then liner 145 will remain longitudinally fixed within shaft 144, and push-pull action will cause core wire 142 to slide within liner 145. Conversely, if the coefficient of friction between liner inner surface 150 and core wire 142 is greater than the coefficient of friction between liner outer surface 151 and the inner wall of shaft 144, then liner 145 will remain longitudinally fixed about core wire 142, and push-pull action will cause shaft 144 to slide over liner 145. The relative coefficients of friction for the movable components of the guidewire assembly may be designed-in by selection of materials and/or coatings, as will be described below. Alternatively, the degree of sliding friction may result from unplanned events, such as the formation of thrombus on one or more component surfaces or embolic debris entering the annular space(s) there between.

Figure 8:
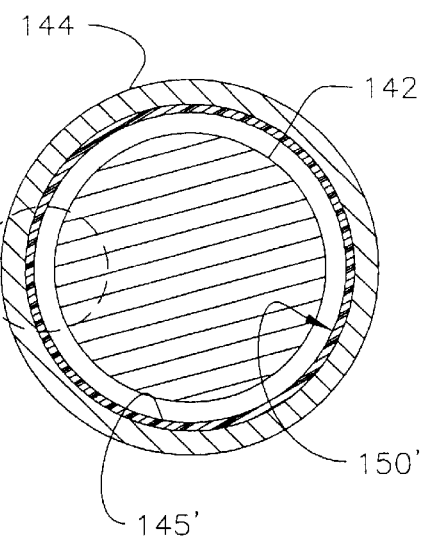
FIG. 8 is a modified form of the cross-sectional view shown in FIG. 7.
Figure 9:
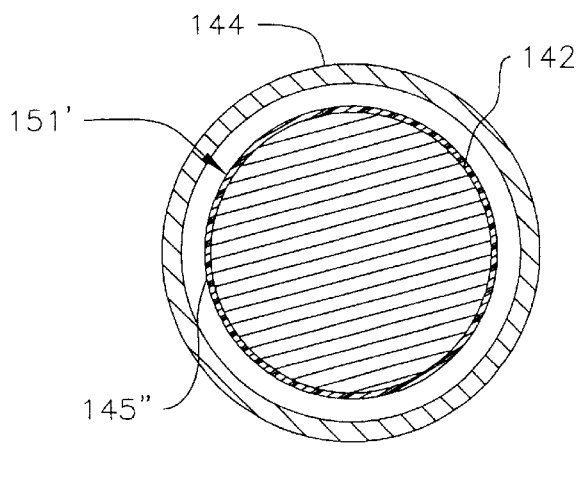
FIG. 9 is another modified form of the cross-sectional view shown in FIG. 7.

FIG. 8 depicts a modified form of the cross-sectional view shown in FIG. 7 in which liner 145' is fitted against the inner wall of shaft 144, leaving radial clearance only between liner inner surface 150' and core wire 142. FIG. 9 depicts another modified form of the cross-sectional view shown in FIG. 7 in which liner 145" is fitted against core wire 142, leaving radial clearance only between liner outer surface 151' and the inner wall of shaft 144.

When filter guidewire 120 is designed for use in small vessels, shaft 144 may have an outer diameter of about 0.36 mm (0.014 inch), and core wire 142 may measure about 0.15 mm (0.006 inch) in diameter. Shaft 144, which can be made from hypo tubing, may have an inside diameter of about 0.23 mm (0.009 inch). For liner 145 to "float" in an annular space between core wire 142 and shaft 144 with such dimensions, liner outer surface 151 may measure about 0.22 mm (0.0088 inch) in diameter and liner inner surface 150 may measure about 0.18 mm (0.0069 inch) in diameter. Liner 145' does not require clearance around its outside diameter, because it is fitted against the inner wall of shaft 144. As compared to liner 145, liner 145' may have a greater wall thickness, and liner inner surface 150' may have a similar inner diameter of about 0.18 mm (0.0069 inch). Liner 145" does not require inside clearance because it is fitted against core wire 142. As compared to liner 145, liner 145" may also have greater wall thickness, and liner outer surface 151' may have a similar outer diameter of about 0.22 mm (0.0088 inch).

Liners 145, 145' and 145" may be formed of polymers selected to provide low coefficients of friction on their sliding surfaces. Typical of such polymers are polytetrafluoroethylene (PTFE), fluorinated ethylene-propylene (FEP), high-density polyethylene (HDPE), and various polyamides (nylons). Alternatively, liners 145, 145' and 145" may be formed of a material selected for physical properties other than a low coefficient of friction, i.e. stiffness or ability to be formed with tight dimensional tolerances. For such materials, a slippery coating, such as silicone, may be applied to the sliding surface(s) in order to achieve the desired low-friction axial bearing properties.

Figure 10:
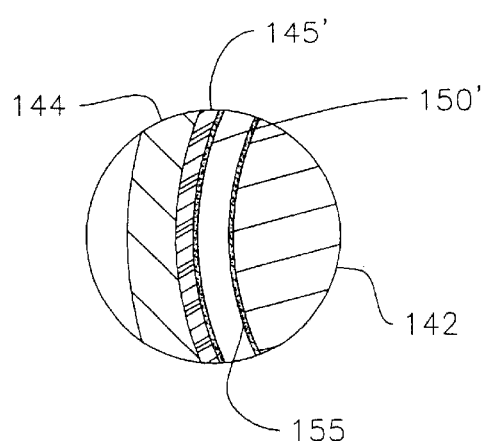
FIG. 10 is an enlarged supplementary view of a portion of FIG. 8, which has been modified to illustrate alternative embodiments of the invention.

Thermoset polyimide (PI) is an example of a liner material that may be selected for properties other than its coefficient of friction. PI tubing is noted for its ability to be formed with tight dimensional tolerances because it is typically formed by building up several layers of cured PI coating around a solid glass core, which is removed by chemical etching. One method of creating a slippery surface on PI tubing is to add a fluoropolymer filler, such as PTFE or FEP, to the PI coating to form one or more low-friction layers at the desired surface(s). Such polyimide/fluoropolymer composite tubing is available from MicroLumen, Inc., Tampa, Fla., U.S.A. FIG. 10 illustrates a modified form of the invention wherein the inner surface of liner 145' comprises lubricious coating 150'. Also shown in FIG. 10 is slippery coating 155, which may be applied to core wire 142 in conjunction with, or instead of, a slippery inner surface of liners 145 or 145'. Coating 155 may comprise a thin film of, for example, silicone or a fluoropolymer.

Another example of a liner material that may be selected for properties other than its coefficient of friction is a block copolymer thermoplastic such as polyethylene block amide (PEBA). Although a slippery coating may be applied to this material, alternatively, plasma-aided surface polymerization may be used to reduce its coefficient of friction. Plasma-aided surface functionalization to achieve high lubricity is described in U.S. Pat. No. 4,693,799 (Yanagihara et al.), and plasma surface modification is available from AST Products, Inc., Billerica, Mass., U.S.A. Plasma treated PEBA may be substituted for PTFE in liners to make use of improved physical properties, including the ability to be plastically extruded.

Figure 11:
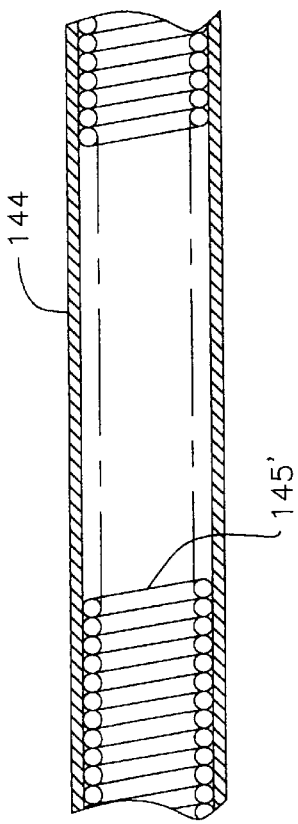
FIG. 11 is a longitudinal sectional view of a segment of a hollow shaft and liner in accordance with the invention.

FIG. 11 depicts a variant of liner 145' disposed within hollow shaft 144. In this example, liner 145' comprises a coiled filament, which may be plastic, metal, or coated or surface-treated forms of either material. The coiled variant may be applied to any of liners 145, 145' or 145", and it provides reduced contact area and concomitantly lower friction as compared to solid tubular liners. Hollow tube 144 and core wire 142 will only touch coiled liner 145' on helical curvilinear portions of the outer and inner surfaces, respectively. If coiled liner 145' is made with an outer diameter larger than the inner diameter of hollow tube 144, then liner 145' will generally hold itself in assembled position against the inner diameter of hollow tube 144. Similarly, if liner 145" is made as a coil with an inner diameter smaller than the diameter of core wire 142, then liner 145" will generally hold itself in assembled position around core wire 142.

FIG. 12 depicts a third embodiment of the invention in which filter guidewire 220 incorporates several elements that are similar to the components of filter guidewires 20 and 120. Core wire 242 is disposed within liner 145, which is disposed within hollow shaft 144. Core wire 242 is comprised of proximal section 256 and separate distal section 258, which extends distally from shaft 144. Sliding clearance(s) may be formed between different elongate movable components, as described above and as shown in FIGS. 7, 8 and 9. If liner 145 is fitted against core wire 242, as shown in FIG. 9, then liner 145 will comprise separate proximal and distal sections (not shown) corresponding to core wire proximal section 256 and core wire distal section 258. Flexible tubular tip member 43 is fixed around the distal end of core wire distal section 258. Transition sleeve 270 is slidably disposed about a distal portion of hollow shaft 144 and extends distally there from to a fixed coupling location on tip member 43. Filter 25 is self-expanding and is positioned generally concentrically with the distal portion of shaft 144. Filter distal end 27 is fixedly coupled to transition sleeve 270, and filter proximal end 29 is fixedly coupled to shaft 144 adjacent the distal portion thereof.

Prior to negotiating vascular anatomy with filter guidewire 220, filter 25 may be collapsed by advancing core wire proximal section 256 within shaft 144 and liner 145 until the distal end of proximal section 256 abuts the proximal end of distal section 258, forming continuous core wire 242. Continued advancement of core wire 242 through shaft 144 and liner 145 will displace tip member 43 distally away from shaft 144. The axial translation of tip member 43 will draw sleeve 270 distally along, but not off of, the distal portion of hollow shaft 144. The relative longitudinal movement of sleeve 270 with respect to shaft 144 causes filter distal end 27 to move away from filter proximal end 29, transforming filter 25 from its expanded configuration to its collapsed configuration. Optionally, filter guidewire 220 may include bends 160 (not shown) in core wire proximal section 256 to provide frictional engagement between core wire 242 and the proximal end of shaft 144. As described above regarding filter guidewire 120, the optional friction mechanism thus created can hold core wire 242 in a selected axial position within shaft 144, thereby retaining filter 25 in the collapsed configuration.

Withdrawing core wire proximal section 256 proximally through shaft 144 and liner 145 allows filter 25 to transform itself towards the expanded configuration by drawing filter ends 27, 29 closer together. The self-transformation of filter 25 towards the expanded configuration causes simultaneous proximal movement of sleeve 270, tip member 43 and core wire distal section 258 relative to shaft 144. The self-expansion of filter 25 stops when a) filter 25 reaches its pre-formed expanded configuration, or b) filter 25 encounters a radial constraint, such as apposition with a vessel wall in a patient, or c) filter 25 encounters an axial constraint, such as the proximal end of sleeve 270 contacting filter proximal end 29, as depicted in FIG. 12. After self-expansion of filter 25 has stopped, any further withdrawal of core wire proximal section 256 will cause it to separate from core wire distal section 258, thereby allowing core wire distal section 258, tip member 43, and sleeve 270 to move freely with respect to the distal end of hollow shaft 144. In this configuration, core wire proximal section 256 will not interfere with self-expansion or self-adjustment of filter 25 in its apposition with the vessel wall.

Transition sleeve 270 may be made of polyimide tubing and may be fixed to tip member 43 and to filter distal end 27 with a suitable adhesive. The length and mounting position of sleeve 270 are selected such that sleeve 270 always surrounds the distal end of shaft 144, regardless of the configuration and length of filter 25. Sleeve 270 can support core wire 242 across the longitudinal gap between the distal end of shaft 144 and the proximal end of tip member 43. By contributing additional stiffness over its length, sleeve 270 also provides a transition in overall stiffness of filter guidewire 220 adjacent the distal end of shaft 144.

FIG. 13 depicts a fourth embodiment of the invention in which occluder guidewire 320 incorporates several elements that are similar to the components of filter guidewires 20, 120, and 220. As distinguished from filter guidewire embodiments of the invention, occluder guidewires are typically used to temporarily obstruct fluid flow through the vessel being treated. Any embolic debris trapped upstream of the occluder element may be aspirated using a separate catheter, with or without irrigation of the area. Core wire 342 is disposed within liner 145, which is disposed within hollow shaft 144. Alternatively, liners 145' or 145" may be substituted for liner 145 such that different sliding clearance(s) may be formed between different elongate movable components, as described above and as shown in FIGS. 7, 8 and 9. Flexible tubular tip member 43 is fixed around the distal end of core 342. Transition sleeve 270 is slidably disposed about a distal portion of hollow shaft 144 and extends distally there from to a sliding coupling location on tip member 43. Proximal stop 381 protrudes radially outward from the proximal end of tip member 43, and distal stop 382 protrudes radially inward from the distal end of transition sleeve 270. Stops 381, 382 interact to prevent the distal end of transition sleeve 270 from sliding proximally off of tip member 43. Proximal stop 381 may comprise a portion of tip member 43, such as one or more enlarged turns at the proximal end of a coil spring. Alternatively, proximal stop 381 may be created with metal or plastic elements, such as solder or polyimide bands. Distal stop 382 may comprise a portion of transition sleeve 270, such as a rim or neck of reduced diameter formed at the distal end thereof. Alternatively, distal stop 382 may be created with metal or plastic elements, such as polyimide rings or bands.

Occluder 325 is self-expanding and is positioned generally concentrically with the distal portion of shaft 144. Similar to filter 25, occluder 325 may comprise a tubular braid, which in this embodiment is coated with an elastic material to render it non-porous. Alternatively, occluder 325 may include self-expanding struts (not shown) that support a non-porous elastic membrane, as known to those of ordinary skill in the art. A non-porous coating or membrane may be made from a variety of elastic materials, such as silicone rubber or a thermoplastic elastomer (TPE). Occluder distal end 327 is fixedly coupled to transition sleeve 270, and occluder proximal end 329 is fixedly coupled to shaft 144 proximally adjacent the distal portion thereof.

In occluder guidewire 320, occluder 325 may be collapsed by advancing core wire 342 through shaft 144 and liner 145, causing tip member 43 to translate within transition sleeve 270 until proximal stop 381 engages distal stop 382, as shown in FIG. 13. Continued advancement of core wire 342 through shaft 144 and liner 145 will displace tip member 43 distally from shaft 144, drawing sleeve 270 along, but not off of, the distal portion of hollow shaft 144. The relative longitudinal movement of sleeve 270 with respect to shaft 144 causes occluder distal end 327 to move away from occluder proximal end 329, which transforms occluder 325 from its expanded configuration to its collapsed configuration. Reversing the above manipulation, i.e. drawing core wire 342 proximally through shaft 144 and liner 145, permits occluder 325 to expand itself. Self-expansion of occluder 325 will stop when one of several conditions is met, as described above with respect to self-expanding filter 25 of filter guidewire 220. Thereafter, continued withdrawal of core wire 342 will draw tip member 43 proximally within transition sleeve 270, creating axial separation (not shown) between stops 381, 382, thereby allowing the distal end of transition sleeve 270, with distal stop 382, to slide freely along tip member 43. In this configuration, core wire 342 and tip member 43 will not interfere with self-expansion or self-adjustment of occluder 325 in its apposition with the vessel wall.

FIG. 13 illustrates the portion of core wire 342 within hollow shaft 144 having a first proximal segment 390, which also extends proximally from hollow shaft 144. First proximal segment 390 is sized to fit slidingly within hollow shaft 144, but without sufficient radial clearance for liners 145, 145' or 145". First proximal segment 390 may comprise a major length of core wire 342, such that relatively short core wire distal segment 391 is dimensioned to receive liners 145, 145' or 145". For example, if occluder guidewire 320 is designed for use in coronary arteries, then the overall length of core wire 342 may be about 175 cm, and the length of core wire distal segment 391 may be about 15 to 25 cm. Alternatively, first proximal segment 390 may have a relatively short length such that core wire distal segment 391 and surrounding liners 145, 145' or 145" extend through a major length of hollow shaft 144.

The transition in diameter between core wire distal segment 391 and first proximal segment 390 may occur as step 398, which can limit the proximal slippage of free-floating liner 145 along core wire 342. Optionally, occluder guidewire 320 may exclude any liner while still incorporating stepped diameter core wire 342 shown in FIG. 13. In such an arrangement, the annular space that would otherwise be occupied by a liner can provide enlarged clearance and accompanying reduced friction between core wire 342 and hollow shaft 144, especially when occluder guidewire 320 is curved through tortuous anatomy. Core wire 342 may also optionally include bends 160 (not shown) located distal to first proximal segment 390.

In order to steer a distal protection guidewire in accordance with the invention through tortuous vasculature, tip member 43 is typically bent or curved prior to insertion of the device, which should transmit to tip member 43 substantially all of the rotation, or torque applied by the clinician at the proximal end of the device. It is most convenient for the physician to steer the device by grasping and rotating shaft 144, and having such rotation imparted to tip member 43, either directly or through the core wire. In distal protection guidewires of the instant invention, various design features reduce longitudinal friction between the hollow shaft and the core wire. These same friction-reducing features also reduce rotational friction between the hollow shaft and the core wire, which would otherwise be useful in transmitting rotation to steer the device. In filter guidewires 20, 120 and 220, torque is transmissible from shaft 144 to tip member 43 through the braided structure of filter 25, however this action is generally effective only when filter 25 is in the collapsed configuration. In occluder guidewire 320, occluder distal end 327 is slidably connected to tip member 43 through transition sleeve 270 such that torque cannot be transmitted from shaft 144 to tip member 43 through occluder 325.

It is therefore advantageous, as shown in occluder guidewire 320, to include a torque-transmitting element, such as torque member 384. Torque member 384 can comprise metal or plastic filaments that form a hollow tube of counter wound spirals or a braid. To minimize bulk and stiffness, torque member 384 may include only a single filament in each of the clockwise and counter clockwise winding directions. The proximal end of torque member 384 is bonded to the distal end of shaft 144 and extends distally there from to surround core wire 342 over a relatively short distance. The distal end of torque member 384 is bonded to the proximal end of tip member 43, or to core wire 342 adjacent thereto. The braided, or spirally wound tubular structure of torque member 384 permits it to transmit rotation forces between shaft 144 and tip member 43, and to do so at any length required to accommodate longitudinal displacement of shaft 144 and tip member 43 during transformation of occluder element 325 between a collapsed configuration and an expanded configuration.

In occluder guidewire 320, second proximal segment 392 is located proximally of first proximal segment 390 and has an enlarged diameter approximating the outer diameter of shaft 144. Reinforcement coil 396 surrounds first proximal segment 390 between second proximal segment 392 and the proximal end of hollow shaft 144. Coil 396 has about the same outer diameter as shaft 144, and helps prevent kinking of the portion of first proximal segment 390 that extends from hollow shaft 144. Reinforcement coil 396 can vary in length to accommodate longitudinal displacement of shaft 144 and core wire 342 during transformation of occluder element 325 between a collapsed configuration and an expanded configuration.

Third proximal segment 394 is located proximally of second proximal segment 392 and is adapted for engagement to a guidewire extension (not shown), as is well known to those of ordinary skill in the art of guidewires. Examples of guidewire extensions usable with occluder guidewire 320 and other embodiments of the invention are shown in U.S. Pat. No. 4,827,941 (Taylor), U.S. Pat. No. 5,113,872 (Jahrmarkt et al.) and U.S. Pat. No. 5,133,364 (Palermo et al.).

FIG. 14 depicts a fifth embodiment of the invention in which occluder guidewire 420 incorporates several elements that are similar to the components of occluder guidewire 320. For example, occluder guidewire 420 has core wire 442 disposed within liner 145, which is disposed within hollow shaft 144. Transition sleeve 270 is slidably disposed about a distal portion of hollow shaft 144 and extends distally there from. Proximal stop 481 protrudes radially outward from core wire 442, and distal stop 482 protrudes radially inward from the distal end of transition sleeve 270. Proximal stop 481 has a maximum transverse dimension, such as an outside diameter, that is greater than a transverse inner dimension, such as an inside diameter, of distal stop 482. Proximal stop 481 is disposed proximal to and is capable of interacting with distal stop 482 to transmit distally directed axial force from core wire 442 to transition sleeve 270.

As illustrated in FIG. 15A, proximal stop 481 may comprise a short coil fixed in the desired position around core wire 442. To increase the strength of the attachment of proximal stop 481 to core wire 442, at least a section of the coil may be longitudinally expanded. The resulting gaps in the coil can be permeated by a suitable bonding material, e.g., solder or adhesive, to both a larger diameter and a greater length, in comparison to unexpanded coils, as shown.

FIG. 15B illustrates a modified form of the stops shown on occluder guidewire 420 in FIG. 14. Proximal stop 481' may be created with metal or plastic elements, such as solder or polyimide bands, as described above regarding occluder guidewire 320. Distal thrust bearing 483 is of the cylindrical, plain, anti-friction type and is disposed about core wire 442 between proximal stop 481' and distal stop 482. Distal thrust bearing 483 serves, as a thrust washer, to reduce rotating friction between stops 481' and 482, especially while occluder 325 is being forced into the collapsed configuration by the push-pull manipulations described above regarding occluder guidewire 320. Reduced rotating friction facilitates turning core wire 442 within collapsed occluder 325, thus providing enhanced steering of occluder guidewire 420 through tortuous curves and branches of a patient's vasculature. Distal thrust bearing 483 may comprise a ring of low-friction material such as a fluoropolymer, a polyamide, HDPE or polyimide/fluoropolymer composite tubing as discussed above regarding liners 145, 145' and 145". Alternatively, distal thrust bearing 483 may comprise a solid ring having a slippery coating applied thereto. Distal thrust bearing 483 may be freely situated in the described location, or it may be fixed to any of the adjacent components such as core wire 442, proximal stop 481' or distal stop 482.

In occluder guidewire 420, occluder 325 is self-expanding and is positioned generally concentrically with the distal portion of shaft 144. Alternatively, filter 25 may be substituted for occluder 325 to create a filter guidewire in accordance with the fifth embodiment of the invention. As described above with respect to occluder guidewire 320, occluder 325 may comprise a tubular braid that is coated with an elastic material to render it non-porous.

Figure 16:
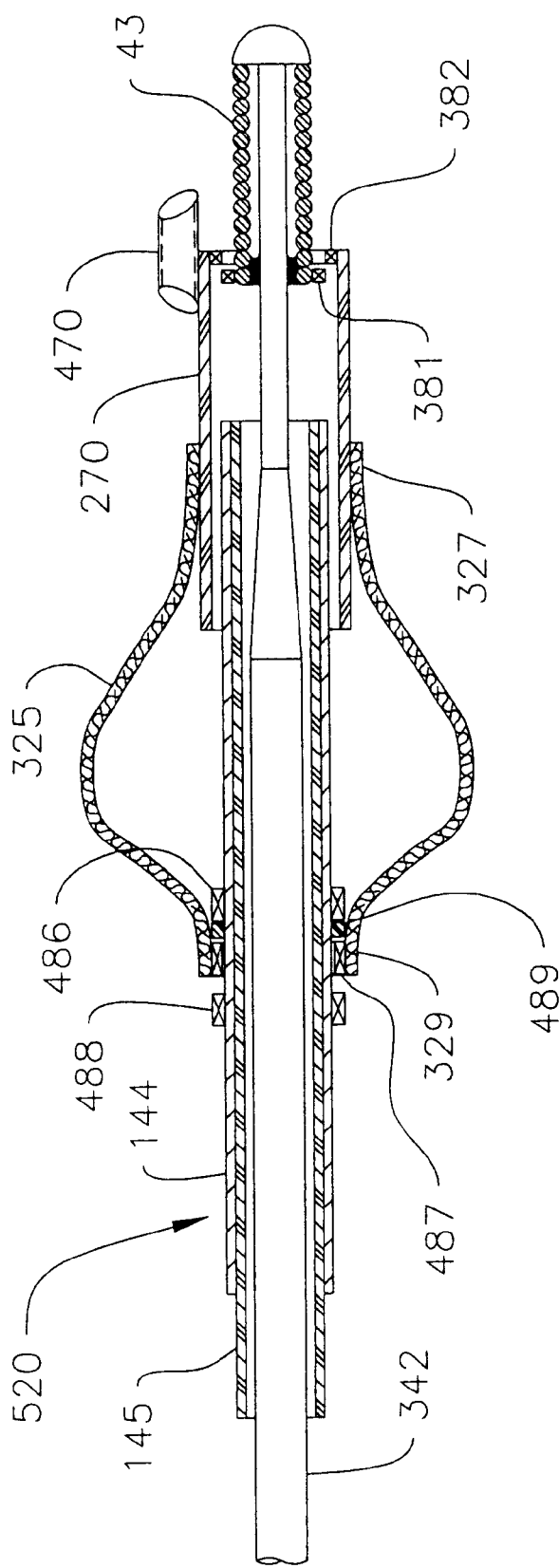
FIG. 16 is a partially sectioned longitudinal view of a sixth guidewire embodiment in accordance with the invention The drawings are not to scale.

As shown in FIG. 14, occluder distal end 327 is fixedly coupled to transition sleeve 270, and occluder proximal end 329 is rotatably coupled to shaft 144 at a location proximally adjacent the distal portion thereof. Occluder proximal end 329 may form a rotatable ring by any suitable means such as heat treatment of the braid, the use of fillers such as solder or adhesives, the addition of an internal or external ring element, or combinations of these methods. For example, FIG. 16 shows slip ring 487 located inside occluder proximal end 329.

In occluder guidewire 420, distal check element 486 protrudes radially outward from shaft 144 distal of occluder proximal end 329. When hollow shaft 144 is drawn proximally over core wire 442, distal check element 486 may contact occluder proximal end 329, to which it may transmit proximally directed force from shaft 144. Optionally, proximal check element 488 protrudes radially outward from shaft 144 proximal of occluder proximal end 329. When hollow shaft 144 is slid distally over core wire 442, proximal check element 488 may contact occluder proximal end 329, to which it may transmit distally directed force from shaft 144. Distal and proximal check elements 486, 488 may comprise rings, bands, coils, pins, adhesive dots, distortions in shaft 144, or any other cooperating features that can effectively check longitudinal movement of occluder proximal end 329 while permitting rotation thereof. Thus, proximal end 329 is rotatable about shaft 144, but may be longitudinally fixed between distal and proximal check elements 486, 488 respectively. Occluder 325 is free to rotate about the supporting steerable guidewire comprising, inter alia, shaft 144 and core wire 442, because transition sleeve 270, with occluder distal end 327 fixed thereto, is also rotatable about the steerable guidewire. Of course, the inverse description may be more clinically significant, i.e., the steerable guidewire can be rotated freely within occluder 325, whether occluder 325 is in the deployed configuration or the collapsed configuration.

Occluder guidewire 420 includes tracking member 470 fixed alongside the distal end of core wire 442. Tracking member 470 is a relatively short tube that is open at both ends and is sized to fit slidably over another guidewire. Tracking member 470 permits occluder guidewire 420 to be guided into a patient's vasculature along with, or by sliding over, another guidewire. Occluder guidewire 420 can also be exchanged easily over an indwelling guidewire. Because tracking member 470 envelopes only a short section of the other guidewire, various types of treatment catheters can be introduced over the other guidewire while occluder guidewire 420 is positioned in the patient. The clinician is thus presented with useful options of advancing therapeutic catheters over occluder guidewire 420, or the other guidewire, or both guidewires.

During use of occluder guidewire 420, occluder 325 may be collapsed by advancing core wire 442 distally through shaft 144 and transition sleeve 270 until proximal stop 481 engages distal stop 482, as shown in FIG. 14. Continued advancement of core wire 442 through shaft 144 will draw sleeve 270 along, but preferably not off of, the distal portion of hollow shaft 144. The relative longitudinal movement of sleeve 270 with respect to shaft 144 causes occluder distal end 327 to separate from occluder proximal end 329, thus transforming occluder 325 from an expanded configuration to a collapsed configuration, as shown in FIG. 14. Reversing the above manipulation, i.e., drawing core wire 442 proximally through shaft 144, permits occluder 325 to expand itself. Self-expansion of occluder 325 will stop when one of several conditions is met, similar to the description above with respect to self-expanding filter 25 of filter guidewire 220. Thereafter, continued withdrawal of core wire 442 will draw its distal end proximally within transition sleeve 270, creating axial separation (not shown) between stops 481, 482, thereby allowing the distal end of transition sleeve 270, with distal stop 482, to slide freely along the distal end of core wire 442 between proximal stop 481 and tracking member 470. Thus, in the deployed configuration of occluder guidewire 420, occluder 325 can self-expand or self-adjust its apposition with the vessel wall.

FIG. 16 depicts a sixth embodiment of the invention in which occluder guidewire 520 incorporates several elements that are similar to the components of occluder guidewires 320 and 420. Elements, and their positions, that are common to occluder guidewires 320 and 520 are shaft 144, liner 145, transition sleeve 270, occluder 325, core wire 342, tip member 43, stops 381, 382, and check elements 486, 488. Occluder guidewire 520 has slip ring 487 fixed within occluder proximal end 329. Slip ring 487 is rotatably mounted about hollow shaft 144 between distal and proximal check elements 486, 488 respectively. The arrangement shown provides unlimited rotation of shaft 144 and core wire 342 within occluder 325, as described above with respect to occluder guidewire 420 Proximal thrust bearing 489 is of the cylindrical, plain, anti-friction type and is disposed about shaft 144 between slip ring 487 and distal check element 486. Proximal thrust bearing 489 serves to reduce friction between slip ring 487 or occluder proximal end 329 and distal check element 486, thus facilitating rotation of shaft 144 within occluder 325, especially when occluder 325 is being forced into the collapsed configuration by the push-pull manipulations described above regarding occluder guidewire 320. Proximal thrust bearing 489 may comprise a ring of low-friction material such as a fluoropolymer, a polyamide, HDPE or polyimide/fluoropolymer composite tubing as discussed above regarding liners 145, 145' and 145". Alternatively, proximal thrust bearing 489 may comprise a solid ring having a slippery coating applied thereto. Proximal thrust bearing 489 may be freely situated in the described location, or it may be fixed to any of the adjacent components such as shaft 144, occluder proximal end 329, distal check element 486 or slip ring 487. It may be especially advantageous to construct an inventive apparatus having a combination (not shown) of distal thrust bearing 483 of occluder guidewire 420 and proximal thrust bearing of occluder guidewire 520.

As shown in FIG. 16, occluder guidewire 520 has tracking member 470 fixed alongside the distal end of the apparatus at the distal end of transition sleeve 270. Since occluder guidewire 520 has both a steerable tip member 43 and tracking member 470, a clinician can choose to insert and steer the device independently through a patient's vasculature, or the clinician can advance the same device over another guidewire. In contrast to occluder guidewire 420, rotation of core wire 342 and tip member 43 does not attempt to revolve core wire 342 around another guidewire, if one is present within tracking member 470. Both occluder guidewires 420 and 520 can be inserted to a desired location over another guidewire, which can then be removed, if so desired. A treatment catheter can be advanced over occluder guidewires 420 and 520 whether the other guidewire has been removed or not.

To adjust and maintain the relative longitudinal and/or rotational positions of core wires and the surrounding hollow shafts in the various embodiments of the invention, a removable handle device (not shown) of a type familiar to those of skill in the art may be used. Such handle devices can have telescoping shafts with collet-type clamps that grip respectively the core wires and shafts in the various embodiments of guidewire apparatuses according to the present invention. The handle device can also serve as a steering handle, or "torquer" which is useful for rotating small-diameter steerable-type guidewires that may be incorporated in the instant invention.

A method of using of a guidewire apparatus of the invention is described as follows. It should be noted that the example described below is unnecessarily limited to a filter guidewire embodiment. Filter guidewire 20, having self-expanding filter 25 and hollow shaft 44 is provided, and advancing core wire 62 through shaft 44 collapses filter 25. With filter 25 in the collapsed configuration, filter guidewire 20 is advanced into the patient's vasculature until filter 25 is beyond intended treatment site 15. Withdrawal of core wire 62 allows filter 25 to expand. With filter 25 deployed into contact with the vessel wall, a therapeutic catheter is advanced over filter guidewire 20 to treatment site 15, and therapy, such as balloon angioplasty, is performed. Any embolic debris generated during the therapy is captured in filter 25. After the therapy is completed, the therapeutic catheter is prepared for withdrawal, as by deflating the balloon, if so equipped. Advancing core wire 62 through shaft 44 collapses filter 25. Finally, filter guidewire 20 and the therapeutic catheter can be withdrawn separately or together, along with collected embolic debris contained within filter 25. If an occluder guidewire of the invention were substituted for a filter guidewire in the above-described method, then aspiration of trapped embolic material would be performed with a separate catheter before collapsing the occluder element.

One benefit of the structures of filter guidewires 20, 120 and 220 is that guidewire tip member 43 forms a fixed length tip of the device, regardless of the configuration of filter 25. Conversely, in occluder guidewire 320, the tip length changes as occluder distal end 327 slides along tip member 43 during transformation of occluder 325 between expanded and collapsed configurations. The variable tip length of occluder guidewire 320 provides a short tip when occluder 325 is collapsed, but the tip needs to lengthen distally of treatment site 15, if possible, during expansion of occluder 325. During deployment of filter guidewires 20, 120 and 220, the distal tip position of the device can remain fixed relative to treatment site 15. This is accomplished by the user holding core wires 42, 142 or 242 anchored relative to the patient, while applying tension to shafts 44 or 144 in the proximal direction. Filter 25 can be maintained in a collapsed configuration by a friction mechanism including bends 160, or by applying proximal tension to shafts 44, 144, thus holding filter proximal end 29 apart from filter distal end 27. Releasing the tension on shafts 44, 144, or advancing them manually, allows filter 25 to expand by filter proximal end 29 translating distally towards filter distal end 27. During this filter deployment, however, the distal tip does not need to move relative to filter 25 or treatment area 15.

While the invention has been particularly shown and described with reference to the preferred embodiments thereof, it will be understood by those skilled in the art that various changes in form and detail may be made there in without departing from the spirit and scope of the invention. For example, the invention may be used in any intravascular treatment utilizing a guidewire and wherein the possibility of loosening emboli exists. Although the description herein illustrates angioplasty and stent placement procedures as significant applications, it should be understood that the present invention is in no way limited to those environments.

We claim:

1. A guidewire apparatus comprising:
   an elongate hollow shaft;
   a core wire movably disposed within the hollow shaft and having a distal end extending there from;
   a transition sleeve slidably disposed about a distal portion of the hollow shaft and the core wire distal end; and
   a tubular protection element having a distal end fixed about the transition sleeve and a proximal end rotatably coupled about the hollow shaft at a location proximal to the distal portion of the hollow shaft, the protection element having a collapsed configuration with a first length and an expanded configuration with a second length shorter than the first length.

2. The guidewire apparatus of claim 1, further comprising a liner interfitted between the core wire and the hollow shaft, the liner having inner and outer surfaces, wherein at least one of the surfaces has a low coefficient of friction.

3. The guidewire apparatus of claim 1, further comprising a tracking member being adapted to slide over another guidewire and being fixed alongside a distal end of the guidewire apparatus.

4. The guidewire apparatus of claim 3, wherein the tracking member is fixed alongside the core wire distal end.

5. The guidewire apparatus of claim 3, further having a flexible tip member fixed about the core wire distal end, wherein the tracking member is fixed alongside a distal end of the transition sleeve.

6. The guidewire apparatus of claim 1, further comprising:
   a distal stop element fixed within a distal end of the transition sleeve; and
   a proximal stop element fixed about the core wire distal end at a location proximal to the distal stop element;
   wherein the proximal stop element has a maximum transverse dimension greater than a transverse inner dimension of the distal stop element.

7. The guidewire apparatus of claim 6, further comprising a distal thrust bearing fitted about the core wire distal end and disposed longitudinally between the distal stop element and the proximal stop element.

8. The guidewire apparatus of claim 6, further comprising a flexible tip member fixed about the core wire distal end and being disposed radially between the core wire distal end and the proximal stop element.

9. The guidewire apparatus of claim 6, wherein the proximal and distal stop elements cooperate to limit sliding of the transition sleeve in a proximal direction along the core wire.

10. The guidewire apparatus of claim 1, further comprising a distal check element fixed about the hollow shaft at a location distal to the protection element proximal end.

11. The guidewire apparatus of claim 10, further comprising a proximal thrust bearing fitted about the hollow shaft and disposed longitudinally between the distal check element and the protection element proximal end.

12. The guidewire apparatus of claim 10, wherein the distal check element limits sliding of the protection element proximal end in a distal direction along the hollow shaft.

13. The guidewire apparatus of claim 1, further comprising a proximal check element fixed about the hollow shaft at a location proximal to the protection element proximal end.

14. The guidewire apparatus of claim 13, wherein the proximal check element limits sliding of the protection element proximal end in a proximal direction along the hollow shaft.

15. The guidewire apparatus of claim 1, wherein the protection element is a filter.

16. The guidewire apparatus of claim 1, wherein the protection element is an occluder.

17. The guidewire apparatus of claim 1, wherein the protection element is self-transformable between the collapsed configuration and the expanded configuration.

* * * * *